United States Patent [19]

Rosenblatt et al.

[11] Patent Number: 4,968,669
[45] Date of Patent: Nov. 6, 1990

[54] PARATHYROID HORMONE ANTAGONISTS

[75] Inventors: Michael Rosenblatt, Ardmore, Pa.; Michael Chorev, Jerusalem, Israel

[73] Assignee: Merck & Co., Inc., Rahway, N.J.

[21] Appl. No.: 341,597

[22] Filed: Apr. 21, 1989

Related U.S. Application Data

[63] Continuation-in-part of Ser. No. 191,512, May 9, 1988.
[51] Int. Cl.$^5$ .................... C07K 7/10; A61K 37/43
[52] U.S. Cl. ........................................ 514/12; 530/324
[58] Field of Search ........................... 530/324; 514/12

[56] References Cited
PUBLICATIONS

Caporale et al. "Characterization of PTH Antagonists". Pept.: Chem. Biol., Proc. Am. Pept. Symp. 10th Mtg. 449–51 (1988).

*Primary Examiner*—Margaret Moskowitz
*Assistant Examiner*—Shelly J. Guest
*Attorney, Agent, or Firm*—Mark R. Daniel; Charles M. Caruso

[57] ABSTRACT

The present invention relates to the use of peptide hormone analogues as inhibitors of their respective naturally occurring peptide hormone. The structure of the peptide hormone analogues is exemplified by parathyroid hormone wherein $Gly^{12}$ is substituted by D-Trp, L-Trp, L- or D- alpha- or beta-naphthylalanine, or D- or L- alpha-MeTrp.

7 Claims, No Drawings

PARATHYROID HORMONE ANTAGONISTS

RELATED APPLICATIONS

This application is a continuation in part of U.S. Ser. No. 191,512, filed May 9, 1988.

BACKGROUND OF THE INVENTION

This invention relates to the use of peptide hormone analogues for inhibiting the naturally occurring hormone peptide in vivo and in vitro. These peptide hormone analogues when administered to a vertebrate, such as mammals, block the endrocrine activity of the peptide hormone or other analogous molecules. These peptide hormone analogues are also useful in vitro in combination with a bioassay for the naturally occurring hormone. The peptide hormone analogues are useful in treating various diseases caused by hormone excess and in treating hormone tumors which secrete hormone-like factors that mimic the hormone actions. One example of this invention relates to the synthesis of parathyroid hormone analogues useful for inhibiting the action of parathyroid hormone both in vivo and in vitro.

Analysis of the relation of structure to hormonal function has provided important insights into the mechanism of action of peptide hormones. Each type of peptide hormone has an affinity for specific receptors to which it binds. Upon binding, the peptide hormone acts either directly or causes a change in the intracellular concentration of a second messenger molecule such as cyclic AMP, cyclic GMP, inositol or calcium ions. These second messenger molecules, in turn, cause changes in the metabolism or physiology of the cell. These changes in cell metabolism or physiology are directly or indirectly dependent upon the binding of the peptide hormone to its specific cell surface receptor. Therefore, if the cell surface receptor is blocked then the hormone effect is also blocked.

Peptide hormone analogues have long been known as a method through which the biochemistry of hormones can be studied and evaluated. Endocrinologists have long desired a method for producing a class of peptide hormone analogues which would allow the blocking of specific hormone receptors without activating a change in the second messenger molecules, thereby avoiding the hormone induced metabolic changes.

Rosenblatt et al., U.S. Pat. No. 4,423,037 and the publications referred to therein describe the structure of certain peptide hormone analogues and their binding to cell receptors. In particular, these publications describe the properties of parathyroid hormone analogues and their physiological properties.

Scientific efforts over a period of many years have sought to understand the interaction between peptide hormones and the cell surface receptor specific for each peptide hormone. One of the peptide hormones, parathyroid hormone, has been studied by using analogues of parathyroid hormone (PTH). One objective of these studies has been to understand the binding of the peptide hormone to the cell surface receptor such that an analogue could be constructed which would bind with the same or greater affinity than the naturally occurring hormone. This would enable the peptide hormone analogue of parathyroid hormone to be used to block the effect of the naturally occurring parathyroid hormone. One of the major problems encountered in this search for a clinically and pharmacologically effective parathyroid hormone analogue was the problem of agonist activity. Agonist activity is the property of the peptide hormone analogue to itself stimulate the change in second messengers which brings about the physiological change associated with the naturally occurring hormone. Therefore, the problem was to create hormone analogues which would bind with high affinity to the appropriate hormone cell surface receptor but not stimulate a change in the second messenger concentration, that is, not act as hormone itself. These analogues could then be used in treating hormone related diseases.

The secondary structure analyses of PTH using Chou Fasman parameters (Chou, P. Y. et al., Biophys, J. 26: 367-373 (1979) does not give a clear indication of a beta-turn or a helix in PTH at the region around position 12. The present invention accomplishes a substitution of amino acids in this region in order to stabilize helix-type or turn-type secondary structural conformations. It is, therefore, a primary object of the present invention to stabilize the bioactive conformation of PTH in order to enhance the biological activity of PTH analogues.

Another object of the present invention is to provide novel PTH analogues. Another object of the present invention is to provide a method of inhibiting the action of PTH through the administration of novel PTH analoges. Still another object of the invention is to provide PTH analogues wherein amino acid modifications result in binding to all the surface receptor without activating the second messenger molecule. The above and other objects are accomplished by the present invention in the manner more fully described below.

SUMMARY OF THE INVENTION

The present invention provides a peptide which comprises PTH(3-34)NH$_2$, [Tyr$^{34}$]PTH (3-34)NH$_2$, [Nle$^{8,18}$,Tyr$^{34}$]PTH(3-34)NH$_2$; PTH(4-34)NH$_2$, [Tyr$^{34}$]PTH(4-34)NH$_2$, [Nle$^{8,18}$,Tyr$^{34}$]PTH(4-34)NH$_2$; PTH(5-34)NH$_2$, [Tyr$^{34}$]PTH (5-34)NH$_2$, [Nle$^{8,18}$,Tyr$^{34}$]PTH(5-34)NH$_2$; PTH(6-34)NH$_2$, [Tyr$^{34}$]PTH-(6-34)NH$_2$, [Nle$^{8,18}$,Tyr$^{34}$]PTH(6-34)NH$_2$; PTH(7-34)NH$_2$, [Tyr$^{34}$]PTH(7-34)NH$_2$, [Nle$^{8,18}$,Tyr$^{34}$]PTH(7-34)NH$_2$ wherein Gly$^{12}$ is substituted by D-Trp, L-Trp, L- or D- alpha- or betanaphthylalanine, or D- or L- alpha- MeTrp. The PTH can be human parathyroid hormone (hPTH), bovine parathyroid hormone (bPTH) or rat parathyroid hormone (rPTH).

Some representative examples of the peptide analogues of the present invention, are as follows: [D-Trp$^{12}$]hPTH(7-34)NH$_2$, [D-Trp$^{12}$,Tyr$^{34}$]hPTH (7-34)NH$_2$, [D-Trp$^{12}$,Nle$^{8,18}$,Tyr$^{34}$]hPTH (7-34)NH$_2$; [L-Trp$^{12}$]hPTH(7-34)NH$_2$, [L-Trp$^{12}$,Nle$^{8,18}$,Tyr$^3$]hPTH(7-34)NH$_2$, [L-Tyr$^{12}$,Tyr$^{34}$]hPTH-(7-34)NH$_2$, [D-Trp$^{12}$]bPTH(7-34)NH$_2$, [D-Trp$^{12}$,Tyr$^{34}$]bPTH(7-34)NH$_2$, [D-Trp$^{12}$,Nle$^{8,18}$,Tyr$^{34}$]bPTH(7-34)NH$_2$; [L-Trp$^{12}$]bPTH(7-34)NH$_2$, [L-Trp$^{12}$,Tyr$^{34}$]bPTH(7-34)NH$_2$,[L-Trp$^{12}$,Nle$^{8,18}$,Tyr$^{34}$]bPTH(7-34)NH$_2$; [D-Trp$^{12}$]rPTH(7-34)NH$_2$, [D-Trp$^{12}$,Tyr$^{34}$]rPTH(7-34)NH$_2$, [D-Trp$^{12}$, Nle$^{8,21}$, Tyr$^{34}$]rPHT(7-34)NH$_2$, [L-Trp$^{12}$]rPTH(7-34)NH$_2$,[L-Trp$^{12}$,Tyr$^{34}$]rPTH(7-34)NH$_2$, [L-Trp$^{12}$,Nle$^{8,21}$,Tyr$^{34}$]rPTH(7-34)NH$_2$. These representative examples should not be construed as limiting the invention.

The present invention also provides a method of inhibiting the action of parathyroid hormone comprising the administration of therapeutically effective amount of a parathyroid hormone analogue described above. The present invention also provides a method of treating osteoporosis or hypercalcemia comprising the administration of a therapeutically effective amount of a parathyroid hormone analogue described above. A method of treating hyperparathyroidism comprising the administration of a therapeutically effective amount of the parathyroid hormone analogues of this invention is also provided. A method of treating hyperparathyroidism expressed as a hypercalcemic crisis, renal failure or hypertension is also provided. A method of treating the disease state produced by a tumor or other cell overproducing a peptide hormone-like molecule and method of treating immune diseases wherein the disease state comprises inflammation, an allergic response, or hyperactive lymphocytes is also provided by the novel peptide hormone analogues of the present invention.

DETAILED DESCRIPTION OF THE INVENTION

Various other objects, features and attendent advantages of the present invention will be more fully appreciated as the same becomes better understood from the following detailed description.

Extensive structure and activity studies have now led to the design of peptide hormone analogues which have high binding affinity for their respective cell surface receptors while not stimulating the production of second messenger molecules. Examples of such a peptide hormone analogues are [D-Trp$^{12}$,Tyr$^{34}$]hPTH-(7-34)NH$_2$ and [D-Trp$^{12}$, Tyr$^{34}$]bPTH(7-34)NH$_2$ which inhibit PTH in vitro but do not act as an agonists.

Agonist activity is dependent upon the presence of the N-terminal amino acid sequence. The removal of two to six end terminal amino acids results in the loss of most if not all agonist activities. Therefore, the second messenger molecules are not affected by those analogues which have the altered amino terminus.

PTH analogues with two to six amino acids removed from the N terminus produces an inhibitor which still binds with high affinity to the peptide hormone receptor without causing a change in cyclic AMP concentration.

The following is the 34-amino acid sequence of bovine parathyroid hormone (bPTH):

H2N-ALA-VAL-SER-GLU-ILE-GLN-PHE-
    MET-HIS-ASN-LEU-GLY-LYS-HIS-LEU(15)-
    SER-SER-MET-GLU-ARG-VAL-GLU-TRP-
    LEU-ARG-LYS-LYS-LEU-GLN-ASP(30)-
    VAL-HIS-ASN-PHE-COOH.

The following is the 34-amino acid sequence of human parathyroid hormone (hPTH):

H2N-SER-VAL-SER-GLU-ILE-GLN-LEU-MET-
    HIS-ASN(10)-LEU-GLY-LYS-HIS-LEU-ASN-
    SER-MET-GLU-ARG(20)-VAL-GLU-TRP-
    LEU-ARG-LYS-LYS-LEU-GLN-ASP(30)-
    VAL-HIS-ASN-PHE-COOH.

The following is the 34-amino acid sequence of rat parathyroid hormone (rPTH):

H2N-ALA-VAL-SER-GLU-ILE-GLN-LEU-
    MET-HIS-ASN(10)-LEU-GLY-LYS-HIS-LEU-
    ALA-SER-VAL-GLU-ARG(20)-MET-GLN-
    TRP-LEU-ARG-LYS-LYS-LEU-GLN-
    ASP(30)-VAL-HIS-ASN-PHE-COOH.

Fragments of peptide hormones containing the region specific for binding to the cell surface receptor can be used as inhibitors or blocking agents. For parathyroid hormone, the N-terminal 34 amino acids are sufficient to define binding specificity to the parathyroid hormone cell surface receptor. This receptor specificity is further defined by the following publication herein incorporated by reference: M. Rosenblatt, et al., Endocrinology, 107:2. 545–550, 1980 and S. R. Nussbaum, et al., Journal of Biological Chemistry, 255:10183, 1980.

The presence of D-amino acids in peptide hormone in place of L-amino acids results in a peptide resistant to catabolism. However, not all such substitutions result in an active peptide hormone. The insertion of tyrosine amide at position 34 in PTH results in a significant increase in the biological activity of the hormone in addition to increasing stability of the peptide. The utilization of D-amino acids in peptide hormone synthesis is described in the following publications herein incorporated by reference: Coltrera, et al., Biochemistry, 19:4380–4385, 1980; Rosenblatt et al., Biochemistry, 20:7246–7250, 1981.

The balance of the description will be divided into two sections. Section I will describe the preparation and structure of inhibitors of peptide hormones, Section II will discuss the use of the peptide hormone inhibitors.

I. Preparation and Structure of Peptide Hormone Inhibitors

The technique of solid-phase peptide synthesis, developed by Merrifield ("Solid Phase Peptide Synthesis", Advances in Enzymology, 32:221–296, 1969) and G. Barany & R. B. Merrifield "Solid Phase Peptide Synthesis" in *The Peptides* Volume 2, editors E. Gross & J. Meienhofen (1980) has been successfully employed in the synthesis of peptide hormones including parathyroid hormone. This method is based on the strategy of having the carboxyl terminus of the peptide linked covalently to a solid support. The desired peptide sequence is prepared by stepwise coupling of single amino acids to a peptide chain growing from the carboxyl toward the amino terminus. Coupling is typically achieved by activation of the carboxyl group of the amino acid being attached to the resin, which may have other potentially reactive groups blocked. Following addition of an amino acid to the growing polypeptide chain, and prior to further chain elongation, the α-amino protecting (BOC) group is typically removed. Because each amino acid is coupled by nearly the same series of reactions, the need for elaborate strategies in the synthesis is minimized. Solubility is not a major issue during synthesis, because the peptide is linked to a solid support. This method is rapid and it can be utilized by a single worker. It is very convenient for the synthesis of multiple analogues with amino terminal substitutions, because a single synthesis can be branched in multiple directions near the amino terminus, thereby creating many analogues varying only in the amino terminal region.

II. Use of Peptide Hormone Inhibitors

The method of inhibiting the action of peptide hormones comprises the administration of a therapeutically effective amount of any peptide hormone or analogue of the present invention. These hormone analogues retain specificity for the cell surface receptor without stimulating a physiological response. This method of use applies to the entire peptide hormone or its analogue, or to a fragment of the peptide hormone containing the receptor binding site.

The use of peptide hormone analogues is exemplified by parathyroid hormone analogues. The parathyroid hormone may be of bovine, human, rat, or any vertebrate origin. The analogue may contain all the amino acids except for the modified N-terminal region or it might comprise the N-terminal 7-34 amino acids. Individual amino acids can be substituted to improve biological or chemical stability as exemplified in the present invention.

The peptide hormone analogues of this invention can be used in vitro to measure the concentration of naturally occurring peptide hormone. This bioassay procedure is illustrated by a bioassay for parathyroid hormone. The unknown concentration of parathyroid hormone in a solution can be determined by measuring the amount of parathyroid hormone analogue required to inhibit its binding to the parathyroid hormone cell surface receptor. The concentration of PTH analogue required to block the action of parathyroid hormone is a direct indicator of the parathyroid hormone concentration.

Parathyroid hormone analogues can be used to diagnose the etiology of or to treat osteoporosis or hypercalcemia through the administration of a therapeutically effective amount of the parathyroid hormone analogues of this invention. Similarly, hyperparathyroidism and other aspects of hyperparathyroidism, such as a hypercalcemic crisis, renal failure or hypertension can be treated through the administration of the parathyroid hormone analogues of this invention.

Tumors and other aberrant cell growth often produce hormone-like substances causing a disease state. The use of peptide hormone analogues to block stimulation caused by such hormone-like substances can result in the alleviation of the disease state. Therefore, the peptide hormone analogues of the present invention can be administered to treat diseases caused by aberrant production of hormone-like substances.

Immune diseases such as inflammation, allergic responses and hyperactive lympocytes can be treated through the administration of peptide hormone analogues which block the action of peptide hormones, such as PTH analogues inhibiting the binding of PTH to cells of the immune system.

The peptide hormone analogues of this invention exhibit both oral and parenteral activity and can be formulated in dosage forms for oral, parenteral, intranasal, or topical administration. Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluent. In the case of capsules, tablets, and pills, the dosage forms may also comprise buffering agents. Tablets and pills can additionally be prepared with an enteric coating.

Liquid dosage forms for oral administration include pharmaceutically acceptable emulsion, solutions, suspensions, syrups and elixers containing inert diluents commonly used in the pharmaceutical art. Besides inert diluents, such compositions can also include adjuvants, such as wetting agents, emulsifying and suspending agents, and sweetening. Preparations according to this invention for parenteral administration include sterile aqueous or non-aqueous solutions, suspensions or emulsions. Examples of non-aqueous solvents or vehicles are propylene glycol, polyethylene glycol, vegetable oils such as olive oil and injectable organic esters such as ethyloleate.

The dosage of active ingredient in the compositions of this invention may be varied; however it is necessary that the amount of the active ingredient shall be such that a suitable dosage form is obtained. The selected dosage form depends upon the desired therapeutic effect, the route of administration, and the duration of the treatment.

Obviously, numerous modifications and variations of the present invention are possible in light of the above teachings. It is therefore to be understood that within the scope of the appended claims, the invention may be practiced otherwise than as specifically described herein.

EXAMPLE 1

Synthesis and Purification of Peptide Hormone Analogues of PTH

Analogues of parathyroid hormone, were prepared by a modification of the solid phase method of Merrifield. Syntheses were performed using an Applied Biosystems 430A Synthesizer. 4-Methylbenzhydrylamine hydrochloride resin (polystyrene-1% by divinylbenzene, USB) was employed as the solid support in order to effect the carboxyamide ($CONH_2$) COOH-terminal modification.

The tertiary butyloxycarbonyl (Boc) group was used to protect the alpha -amino group of each amino acid during coupling. Side-function protection was afforded as follows: (a) the hydroxyl group of serine was protected as the O-benzyl ether (BZL); (b) the hydroxyl group of tryosine as the 0-2,6dichlorobenzyl ether (DCB) or p-bromobenzyloxycarbonyl ester (BrZ); (c) the carboxyl group of glutamic and aspartic acid as the benzyl (BZ) or cyclohexyl ester (Chx); (d) the imidazole nitrogen of histidine by the benzyloxymethyl (BOM) and the guanidine function of arginine was protected by the p-toluene-sulfonyl (TOS) group, and the indole imine by formyl groups (FOR); and (e) the lysine epsilon amino group by 2-chlorobenzylcarbonyl (CLZ). All amino acids were obtained from Applied Biosystems, Inc., Peninsula Laboratories, or Bachem Chemicals.

The peptide-resin synthesis were carried out using Applied Biosystems, Inc. specified protocols. Double couplings were carried out for the incorporation of each amino acid. Deprotection times with trifluoroacetic acid were extended 6 minutes over manufacturer protocols.

The peptide was cleaved from the copolymer resin with simultaneous removal of the side-chain protecting groups similar to the 2 step HF cleavage procedure described by Tam, J.A.C.S. 105: 6442-6455 (1983). In the first HF step the following ratios of reagents were used: 5% p-cresol, 5% p-thiocresol, 65% dimethyl sulfide and 25% HF. 10 ml of mixture per gram of peptide-resin was used for 2 hours at 0° C. In the second HF step the following ratio of reagents were used: 5% p-cresol, 5% p-thiocresol and 90% HF. The cleavage was carried out for 75 min. at 0° C. After removal of HF the peptide-resin mixture was washed with anhydrous ether to remove scavenger. The peptide was then extracted with 50% acetic acid and water. The washes were combined and chromatographed using Sephadex G 50F, eluting with 50% HOAc.

After lyophilization, the partially Purified peptide was chromatographed by reverse phase HPLC (Vydac C4 bonded silica, 15 u particle size, 300 Å pore size, using aqueous acetonitrile gradient containing 0.1% TFA).

EXAMPLE 2

PTH Binding Assay Results

PTH analogues were analysed in a new receptor assay (Goldman et al., Endocrin. (1988) 123:1468–1475) which modified the assay reported in Rosenblatt et al., Endocrin. 107: 545–550 (1980). The binding assay used [Nle$^{8,18}$, $^{125}$I-Tyr$^{34}$]bPTH (1–34)NH$_2$ which was purified by HPLC (Novapak C$_{18}$, 32–35% CH$_3$CN in 0.1% TFA) and was stored as aliquots in 25 mM TrisHCl/1% BSA at −70° C. Bovine renal cortical plasma membranes were incubated with radioligand (25,000 cpm) in the absence or presence of PTH analogues in a Tris containing buffer (250 μl) for 30 min. at 21° C. Once equilibrium was reached, bound and free radioligand were separated by centrifugation. High specific binding (85%) to bovine renal cortical membranes was obtained consistently.

TABLE

| Structure | Binding $K_I$(nM) |
|---|---|
| [D—Trp$^{12}$,Tyr$^{34}$]bPTH(7–34)NH$_2$ | 8 ± 1 |
| [Nle$^{8,18}$,D—Trp$^{12}$,Tyr$^{34}$]bPTH(7–34)NH$_2$ | 13 ± 3 |
| [Tyr$^{34}$]bPTH(7–34)NH$_2$ | 76 ± 9.0 |
| [Nle$^{8,18}$,Trp$^{34}$]bPTH(7–34)NH$_2$ | 145 ± 13 |
| [Trp$^{12}$,Tyr$^{34}$]bPTH(7–34)NH$_2$ | 106 ± 9 |
| [Nle$^{8,18}$,Trp$^{12}$,Tyr$^{34}$]bPTH(7–34)NH$_2$ | 51 ± 3 |

EXAMPLE 3

ROS 17/2.8 ASSAY RESULTS

PTH analogues were analyzed in a rat osteosarcoma cell line (ROS 17/2.8) for their ability to inhibit cyclic AMP stimulation by 1 nM [Nle$^{8,18}$,Tyr$^{34}$]bPTH-(1–34)NH$_2$ by the method described in R. J. Majeska et al, Endocrinol. 107, 1494 (1980). Briefly ells, preloaded with [$^3$H] adenine were incubated with the agonist PTH(1–34) in the presence or absence of the PTH analogue for 5 minutes at 37° C. in the presence of IBMX (phoaphodiesterase inhibitor). The formation of [$^3$H] cAMP was followed to determine the effect of the pTH analogue.

| Structure | Adenylate Cyclase $K_I$(nM) |
|---|---|
| [D—Trp$^{12}$,Tyr$^{34}$]bPTH(7–34)NH$_2$ | 211 ± 116 |
| [D—Trp$^{12}$,Nle$^{8,18}$,Tyr$^{34}$]bPTH(7–34)NH$_2$ | 69 ± 17 |
| [Tyr$^{34}$]bPTH(7–34)NH$_2$ | 2720 ± 520 |

EXAMPLE 4

Bovine Renal Membrace Adenylate Cyclase

PTH analogues were evaluated for their effects on the stimulation of cyclic AMP production by bovine renal membranes stimulated with 3nM [Nle$^{8,18}$,Tyr$^{34}$]bPTH-(1–34)NH$_2$. Bovine renal membranes were incubated with agonist in the presence or absence of the PTH analogue at 30° C for 30 min. Cyclic AMP produced was measured as described (B. L. Brown et. al., Adv. Cyclic Neucleotide Res. 2,24 (1972)).

| Structure | Adenylate Cyclase $K_I$(nM) |
|---|---|
| [D—Trp$^{12}$,Tyr$^{34}$]bPTH(7–34)NH$_2$ | 69 ± 5 |
| [Nle$^{8,18}$,D—Trp$^{12}$,Try$^{34}$]bPTH(7–34)NH$_2$ | 125 ± 7 |
| [Tyr$^{34}$]bPTH(7–34)NH$_2$ | 880 ± 70 |
| [Nle$^{8,18}$,Tyr$^{34}$]bPTH(7–34)NH$_2$ | 1631 ± 350 |
| [Trp$^{12}$,Tyr$^{34}$]bPTH(7–34)NH$_2$ | 737 ± 105 |

EXAMPLE 5

PTH Binding Assay Results

PTH analogs were analyzed for their ability to inhibit I$^{125}$-labeled PTH binding to the bone-derived rat osteosarcoma cell line ROS 17/2.8 as described in McKee, R. et al., Endocrinology (1988) 122 (6): 3008–10. The results are as follows:

| Structure | Binding $K_I$(nM) |
|---|---|
| [D—Trp$^{12}$,Tyr$^{34}$]bPTH(7–34)NH$_2$ | 123 |
| [Nle$^{8,18}$,D—Trp$^{12}$,Tyr$^{34}$]bPTH(7–34)NH$_2$ | 182 ± 32 |
| [Nle$^{8,18}$,Tyr$^{34}$]bPTH(7–34)NH$_2$ | 964 ± 170 |
| [Trp$^{12}$,Tyr$^{34}$]bPTH(7–34)NH$_2$ | 397 ± 21 |
| [Tyr$^{34}$]bPTH(7–34)NH$_2$ | 700 ± 90 |

EXAMPLE 6

PTH-binding Assay Results (Canine Kidney)

PTH analogues were assayed for their ability to inhibit I$^{125}$-labeled PTH binding to canine renal certical membranes in an assay similar to that described in Example 2.

| Structure | Binding $K_I$(nM) |
|---|---|
| [Tyr$^{34}$]bPTH(7–34)NH$_2$ | 45.8 ± 11.3 |
| [D—Trp$^{12}$,Tyr$^{34}$]bPTH(7–34)NH$_2$ | 0.38 ± 0.14 |

EXAMPLE 7

PTH-binding Assay Results (Human osteosarcoma cells)

PTH analogues were assayed for their ability to inhibit I$^{125}$-labeled PTH binding to human osteosarcoma cells (BIO) in a manner similar to that described in Example 5.

| Structure | Binding $K_I$(nM) |
|---|---|
| [Tyr$^{34}$]bPTH(7–34)NH$_2$ | 5.5 ± 1.6 |
| [D—Trp$^{12}$,Tyr$^{34}$]bPTH(7–34) | 3.5 ± 1.6 |

What is claimed is:

1. A peptide having the formula PTH(7–34)NH$_2$, (Tyr$^{34}$)PTH(7–34)NH$_2$ or (Nle$^{8,18}$,Tyr$^{34}$)PTH(7–34)NH$_2$, wherein Gly$^{12}$ is substituted by D-Trp.

2. A peptide according to claim 1, wherein PTH is rPTH, bPTH or hPTH.

3. A peptide according to claim 2 which is [D-Trp$^{12}$]hPTH(7–34)NH$_2$, [D-Trp$^{12}$,Tyr$^{34}$]hPTH-(7–34)NH$_2$ or [D-Trp$^{12}$,Nle$^{8,18}$,Tyr$^{34}$]hPTH(7–34NH$_2$.

4. A peptide according to claim 2 which is [D-Trp$^{12}$]bPTH(7–34)NH$_2$, [D-Trp$^{12}$,Tyr$^{34}$]bPTH-(7–34)NH$_2$ or [D-Trp$^{12}$,Nle$^{8,18}$,Tyr$^{34}$]bPTH(7–34)NH$_2$.

5. A peptide according to claim 2 which is [D-Trp$^{12}$]rPTH(7–34)NH$_2$, [D-Trp$^{12}$,Tyr$^{34}$]rPTH-(7–34)NH$_2$ or [D-Trp$^{12}$,Nle$^{8,18}$,Tyr$^{34}$]rPTH(7–34)NH$_2$.

6. A method of acting upon a PTH receptor which comprises administering a hypercalcemia treating effective amount of a peptide of claim 1 to a mammal.

7. A pharmaceutical composition which comprises a hypercalcemia treating effective amount of a peptide of claim 1 and a pharmaceutically acceptable carrier.

* * * * *